United States Patent
Ahn et al.

(10) Patent No.: US 11,015,163 B2
(45) Date of Patent: May 25, 2021

(54) CELL PRINTING APPARATUS

(71) Applicants: T&R BIOFAB CO., LTD., Gyeonggi-do (KR); Korea Polytechnic University Industry Academic Cooperation Foundation, Gyeonggi-do (KR)

(72) Inventors: Geunseon Ahn, Gyeonggi-do (KR); Jinhyung Shim, Gyeonggi-do (KR); Kyunghyun Min, Gyeonggi-do (KR); Wonsoo Yun, Gyeonggi-do (KR); Songwan Jin, Gyeonggi-do (KR)

(73) Assignees: T&R BIOFAB CO., LTD., Gyeonggi-do (KR); KOREA POLYTECHNIC UNIVERSITY INDUSTRY ACADEMIC COOPERATION FOUNDATION, Gyeonggi-do (KR)

( * ) Notice: Subject to any disclaimer, the term of this patent is extended or adjusted under 35 U.S.C. 154(b) by 222 days.

(21) Appl. No.: 16/028,913

(22) Filed: Jul. 6, 2018

(65) Prior Publication Data

US 2018/0312795 A1  Nov. 1, 2018

Related U.S. Application Data

(63) Continuation of application No. PCT/KR2017/000131, filed on Jan. 5, 2017.

(30) Foreign Application Priority Data

Jan. 7, 2016  (KR) .................. 10-2016-0002012

(51) Int. Cl.

| | |
|---|---|
| *C12M 1/02* | (2006.01) |
| *B33Y 30/00* | (2015.01) |
| *C12N 11/00* | (2006.01) |
| *B29C 64/30* | (2017.01) |
| *C12M 1/26* | (2006.01) |
| *B29C 64/364* | (2017.01) |

(Continued)

(52) U.S. Cl.
CPC ............. *C12M 41/24* (2013.01); *B29C 64/30* (2017.08); *B29C 64/364* (2017.08); *B33Y 30/00* (2014.12);

(Continued)

(58) Field of Classification Search
CPC ..... B29C 64/364; B29C 64/30; B29C 64/295; B29C 64/106
See application file for complete search history.

(56) References Cited

U.S. PATENT DOCUMENTS 9,771,554 B2 *  9/2017  Morgan ................. C12M 21/08
2003/0090034 A1  5/2003  Mulhaupt et al.
(Continued)

FOREIGN PATENT DOCUMENTS

WO  2015/066705 A1  5/2015

OTHER PUBLICATIONS

Landers, R. et al., "Rapid prototyping of scaffolds derived from thermoreversible hydrogels and tailored for applications in tissue engineering", Biomaterials, 23 (2002) pp. 4437-4447.

(Continued)

*Primary Examiner* — Jacob T Minskey
*Assistant Examiner* — Virak Nguon
(74) *Attorney, Agent, or Firm* — Nelson Mullins Riley & Scarborough LLP; Kongsik Kim, Esq.

(57) ABSTRACT

A cell printing apparatus according to the present disclosure comprises: a nozzle through which a liquid cell substance is discharged; a container in which the liquid cell substance discharged through the nozzle is laminated into a three-dimensional structure; and a supply unit for supplying the liquid heated to a predetermined temperature to the container.

5 Claims, 3 Drawing Sheets

(a)

(b)

(51) Int. Cl.
  *B33Y 40/00* (2020.01)
  *C12M 3/00* (2006.01)
  *B29C 64/106* (2017.01)
  *B29C 64/295* (2017.01)
  *B33Y 10/00* (2015.01)

(52) U.S. Cl.
  CPC ............ *B33Y 40/00* (2014.12); *C12M 21/08* (2013.01); *C12M 33/00* (2013.01); *C12N 11/00* (2013.01); *B29C 64/106* (2017.08); *B29C 64/295* (2017.08); *B33Y 10/00* (2014.12)

(56) References Cited

U.S. PATENT DOCUMENTS

| | | | | |
|---|---|---|---|---|
| 2014/0273191 A1* | 9/2014 | Tipgunlakant | ........... | C12Q 1/02 435/288.4 |
| 2015/0037445 A1* | 2/2015 | Murphy | ................. | C12M 41/00 425/131.1 |
| 2018/0304537 A1* | 10/2018 | Rubinsky | ............... | B33Y 10/00 |
| 2020/0247053 A1* | 8/2020 | Rodriguez | ............ | B29C 64/118 |

OTHER PUBLICATIONS

Gao, Q. et al., "Coaxial nozzle-assisted 3D bioprinting with built-in microchannels for nutrients delivery", Biomaterials, 61 (2015) pp. 203-215.

Khatiwala, C. et al., "3D Cell Bioprinting for Regenerative Medicine Research and Therapies", Gene Therapy and Regulation, vol. 7, No. 1 (2012) 19 pages.

Skardal, A. "Biomaterials for Integration with 3-D Bioprinting", Annals of Biomedical Engineering, vol. 43, No. 3 (Mar. 2015) pp. 730-746.

* cited by examiner (a)

(b)

(a)

(b)

(a)

(b)

CELL PRINTING APPARATUS

CROSS-REFERENCE TO RELATED APPLICATION

This application is a continuation of International Application No. PCT/KR2017/000131 filed on Jan. 5, 2017, which claims priority to Korean Application No. 10-2016-0002012 filed on Jan. 7, 2016. The applications are expressly incorporated herein by reference.

TECHNICAL FIELD

The present disclosure relates to a cell printing apparatus, and particularly, to a cell printing apparatus where a 3D structure is quickly cured so that the lamination of the 3D structure is smoothly carried out.

BACKGROUND

There has been a lot of studies for fabricating tissue structures by 3D printing technique. The technique is referred to as "cell printing" where a liquid cell substance such as collagen, or dECM (decellurized extracellular matrix) which contains cells and is in as gel state, is discharged from a nozzle of a 3D bio-printer to be printed. In this specification, the term "liquid cell substance" means a liquid substance such as collagen, dECM, hydrogel and the like which contains cells and is discharged for the purpose of 3D cell printing.

The liquid cell substance is maintained in a liquid state at a temperature lower than a first temperature but is cured at a temperature of a second temperature or higher, the second temperature being higher than the first temperature.

In the event that the liquid cell substance is discharged by the 3D bio-printer to laminate a cell structure on a bottom, if the temperature of the liquid cell substance is lower than the second temperature, layers of the liquid cell substance may slip down in a state of being not cured, and thus the laminated structure collapses. Therefore, there is a problem in that the liquid cell substance cannot be printed as the desired 3D structure.

In order to solve the problem, a heat source is provided under the bottom on which the structure is laminated by the 3D cell printing apparatus so that the liquid cell substance is heated to a gelation temperature or higher.

The conventional method has a problem in that if the structure becomes higher in the process of continuously laminating the 3D structure, the heat of the heat source cannot not be properly transferred to the upper layer of the liquid cell substance from the bottom so that it does not reach the gelation temperature.

Another method of cell-printing in a liquid bath is known. In this method, a lot of cell culture mediums should be used, and the risk of cell contamination increases. If the liquid bath is filled with a liquid, a cell layer does not properly adhere to the bottom of the liquid bath when the first layer is discharged, and thus it is not possible to create a precise 3D cell structure in practice.

SUMMARY

The object of the present disclosure is to provide a cell printing apparatus, in which a liquid cell substance is quickly cured regardless of a height of laminated layers.

The cell printing apparatus of the present disclosure comprises a nozzle configured to discharge a liquid cell substance; a container where the liquid cell substance discharged from the nozzle is laminated in a 3D structure; and a supply unit for supplying a heated liquid to the container.

Preferably, a temperature of the liquid is a gelation temperature or higher to gel the liquid cell substance discharged from the nozzle.

Preferably, the supply unit supplies the heated liquid at a height enough to expose the top portion of the 3D structure.

Preferably, the liquid is a cell culture medium.

Preferably, the supply unit starts to supply the heated liquid after a first layer of the liquid cell substance is laminated.

Preferably, the cell printing apparatus further comprises a heating unit for heating the container.

According to the present disclosure, it is very advantageous to fabrication of the 3D structure since the liquid cell substance discharged from the nozzle is cured simultaneously with the lamination.

DETAILED DESCRIPTION

Hereinafter, the present disclosure will be described in detail with reference to the accompanying drawings.

Figure 1:
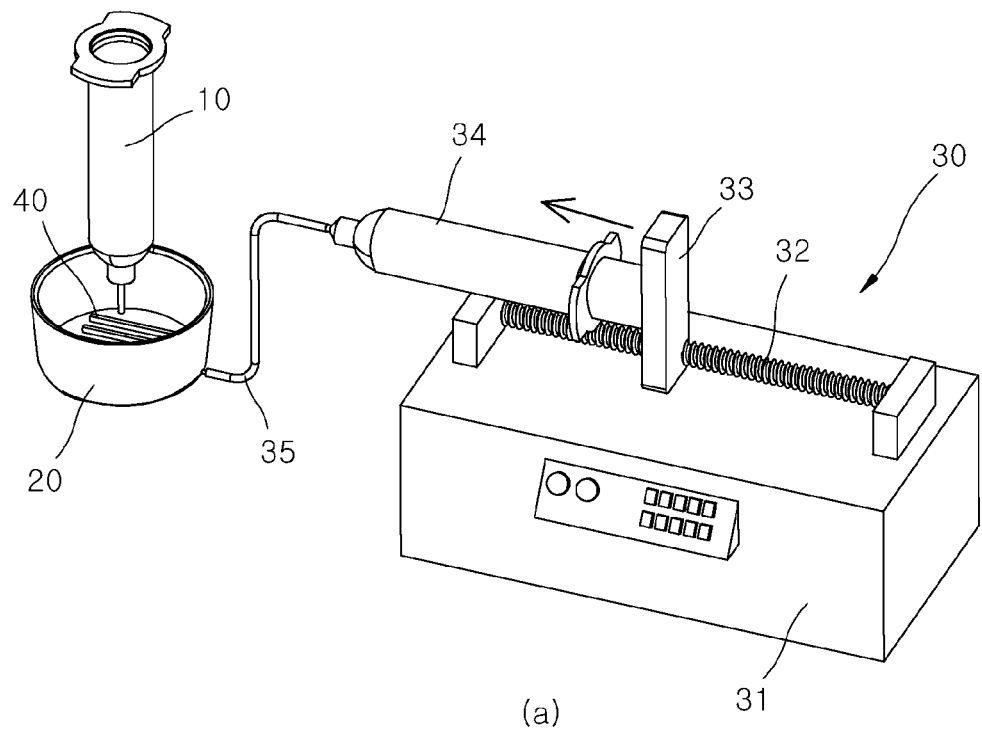
FIG. 1 is a view showing a state in which a first layer is laminated by a cell printing apparatus according to an embodiment of the present disclosure.
Figure 1:
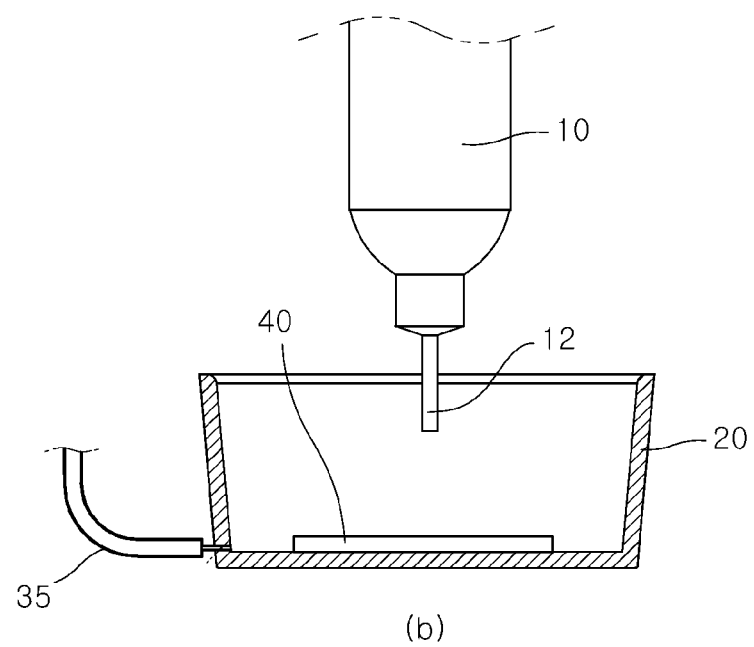

FIG. 1 is a view schematically showing a state in which a first layer is laminated by a cell printing apparatus according to an embodiment of the present disclosure. As illustrated in FIG. 1, the cell printing apparatus of this embodiment comprises a nozzle unit (10) for discharging a liquid cell substance, a container (20) where a liquid cell substance discharged from the nozzle unit (10) is laminated to create a 3D structure (40), and a supply unit (30) for supplying a liquid (50) heated to a predetermined temperature into the container (20). The supply unit (30) has a controller (31), a liquid storage (34) and a supply pipe (35). In the supply unit (30) in FIG. 1 which is shown non-limitedly and exemplarily, a piston (33) moves along a guide member (32) to control a supply amount of the heated liquid. Any known liquid supply devices may be used as the supply unit (30) for supplying the heated liquid. It should be appreciated that the scope of the present disclosure is not limited to the configuration shown in FIG. 1.

In the supply unit (30) shown in FIG. 1 which is shown non-limitedly and exemplarily, the piston (33) moves along the guide member (32) in an arrow direction to supply the liquid stored in the fluid storage (34) to the container (20) via the supply pipe (35) under the control of the controller (31).

Figure 2:
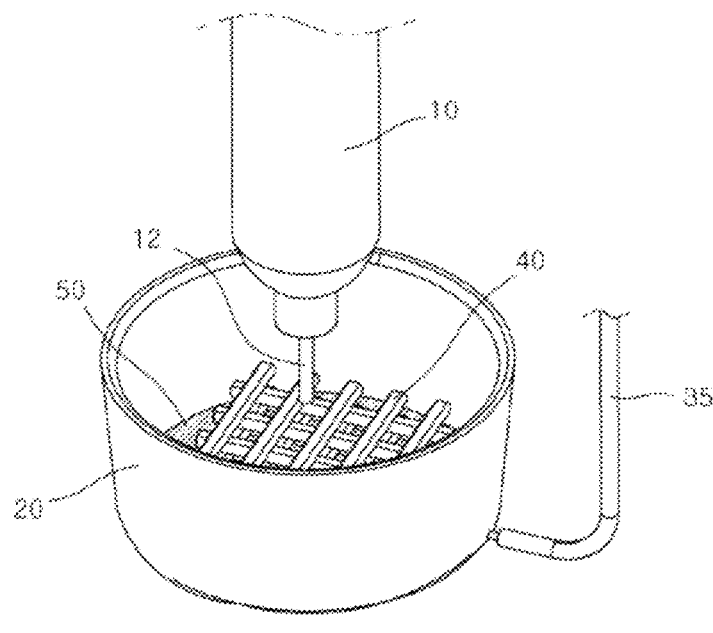
FIGS. 2 and 3 are views showing a state in which a heated liquid is supplied, in a state of being further laminated on the first layer in FIG. 1.
Figure 2:
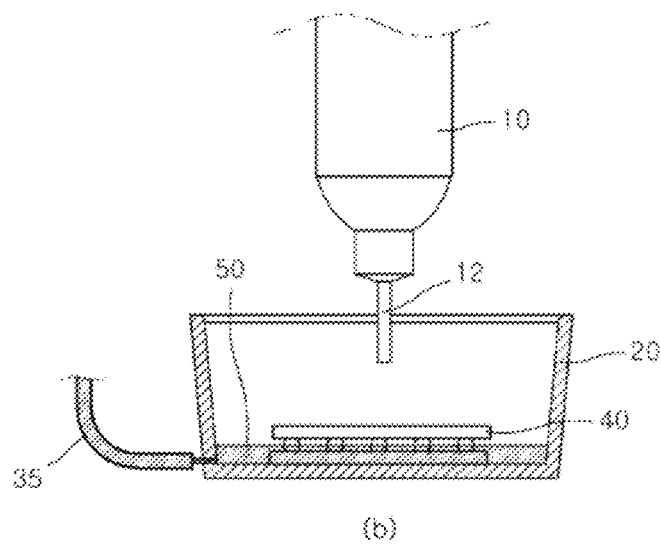
Figure 3:
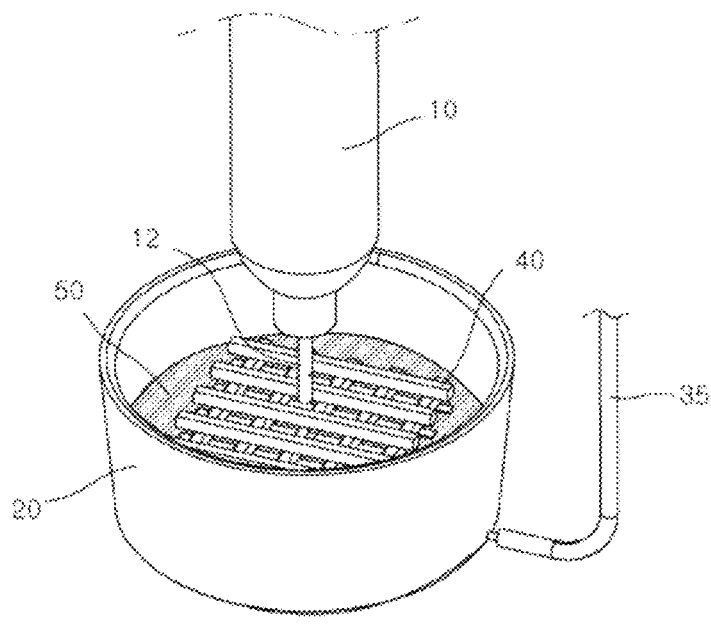
Figure 3:
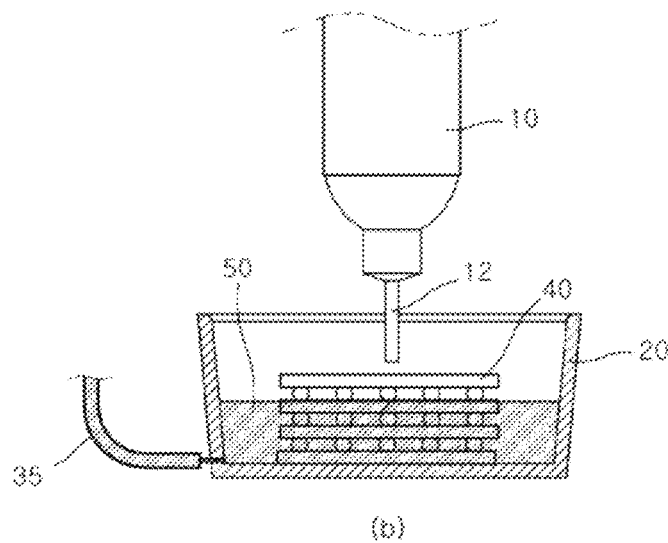

The liquid cell substance is discharged from the nozzle (12) and is laminated on the bottom of the container (20). After a first layer is laminated as shown in FIG. 1b, and then further layers are consecutively laminated thereon to form a 3D structure (40). Preferably, the heated liquid is not supplied to the container (20) before the first layer is laminated. The heated liquid may be supplied to the container (20) via the supply pipe (35) as the liquid cell substance is laminated on the first layer. It is preferable to supply the heated liquid to the container (20) at a height enough to expose the top portion of the 3D structure. FIGS. 2 and 3 are views showing a heightened 3D structure (40) and the heated liquid which is supplied at the height enough to expose the top portion of the structure.

A heating unit (not shown) for maintaining the container (20) at a predetermined temperature may be provided. The heating unit may be any one of various known heat sources, such as a heating wire, a heating plate or an infrared lamp.

The liquid supplied to the container 20 may be a cell culture medium.

According to the present disclosure, it is very advantageous to fabricate a 3D structure since the liquid cell substance discharged from the nozzle is cured simultaneously with the lamination.

While the present disclosure has been described with reference to the accompanying drawings, it should be appreciated that the scope of the present disclosure is determined by the appended claims and that the scope is not limited to the embodiments and/or the drawings. It is to be appreciated that a person skilled in the art can change or modify the embodiments without departing from the scope and spirit of the present disclosure.

The present invention was supported by Priority Research Centers Program through the National Research Foundation of Korea (NRF) funded by the Ministry of Education, Science and Technology (2017R1A6A1A03015562).

The invention claimed is:

1. A cell printing apparatus comprising:
   a nozzle configured to discharge a liquid cell substance;
   a container where the liquid cell substance discharged from the nozzle is laminated to create a 3D structure; and
   a supply unit for supplying a heated liquid to the container, wherein the heated liquid cures the liquid cell substance,
   wherein the supply unit is configured to regulate an amount of the heated liquid supplied to the container to cause a top portion of the 3D structure to be exposed and a remaining portion of the 3D structure to be submerged.

2. The cell printing apparatus according to claim 1, wherein the heated liquid is heated to a gelation temperature to gel the liquid cell substance discharged from the nozzle.

3. The cell printing apparatus according to claim 1 or 2, wherein the heated liquid is a cell culture medium.

4. The cell printing apparatus according to claim 1 or 2, wherein the supply unit starts to supply the heated liquid after a first layer of the liquid cell substance is laminated.

5. The cell printing apparatus according to claim 1 or 2, further comprising a heating unit for heating the container.

* * * * *